United States Patent [19]

Gherardi et al.

[11] 4,190,654

[45] Feb. 26, 1980

[54] PHARMACEUTICAL COMPOSITION COMPRISING ANXIOLYTIC DRUGS AND BETA-ADRENERGIC RECEPTOR BLOCKING AGENTS

[75] Inventors: Paolo Gherardi; Giorgio Ferrari, both of Milan, Italy

[73] Assignee: Simes Societa Italiana Medicinali e Sintatici S.p.A., Milan, Italy

[21] Appl. No.: 935,721

[22] Filed: Aug. 21, 1978

[30] Foreign Application Priority Data

Aug. 29, 1977 [BE] Belgium ............................. 180506

[51] Int. Cl.² .................. A61K 31/33; A61K 31/135
[52] U.S. Cl. ..................................... 424/244; 424/330
[58] Field of Search ............................ 424/244, 330

[56] References Cited

U.S. PATENT DOCUMENTS 3,867,529  2/1975  Ferrari et al. ..................... 424/244

OTHER PUBLICATIONS

Chem. Abst., vol. 71, 30165r, (1969).

Primary Examiner—Stanley J. Friedman
Attorney, Agent, or Firm—Cushman, Darby & Cushman

[57] ABSTRACT

A pharmaceutical composition for the therapeutical treatment of anxiety and neurodystonic states characterized by combining an anxiolytic belonging to the class of the benzodiazepines and a beta-adrenergic receptor blocking agent, in which said benzodiazepinic anxiolytic is 3-N,N-dimethylcarbamoyloxy-1-methyl, 5-phenyl, 7-chloro, 1,3-dihydro-2H-1,4-benzodiazepin-2-one- and said beta-adrenergic receptor blocking agent is 1-(0-methoxyphenoxy)-3-isopropylamino-propan-2-olo.

6 Claims, No Drawings

PHARMACEUTICAL COMPOSITION COMPRISING ANXIOLYTIC DRUGS AND BETA-ADRENERGIC RECEPTOR BLOCKING AGENTS

The invention concerns pharmaceutical compositions suitable for the therapeutic treatment of anxious and neurodystonic states characterized by an excessive functional response of the cardiovascular system and other physiological systems to stress.

In particular, the invention concerns the treatment of such morbid states by the use of a combination of drugs each having a different mechanism of action, but synergic, so as to obtain a better and more complete therapeutic result than that given by a mere summation of the effects of the two drugs administered singly.

It has been found that especially significant results, in the aforesaid sense, are obtained by combining suitable doses of an anxiolytic belonging to the class of the benzodiazepines, such as, for example, 3-N,N-dimethylcarbamoyloxy-1-methyl,5-phenyl, 7-chloro, 1,3-dihydro-2H-1,4-benzodiazepin-2-one with a beta-adrenergic receptor/blocking agent, such as, for example 1-(o-methoxyphenoxy)-3-isopropyl amino-propan-2-ol hydrochloride.

The pharmaceutical dosage forms pertinent to the invention are especially those for oral administration and comprise variable proportions and doses of the two drugs incorporated in suitable excipients also to obtain sustained release preparations.

In anxiety states there is hyperactivity of the sympathetic nervous system and this accompanies an increased turnover and excretion of catecholamines; it is in fact known that anxious individuals have a higher catecholamine excretion rate that normal individuals. The elevated sympathetic tone causes the onset of a wide variety of prevalently somatic symptoms, which, in turn, contribute to maintaining, if not even to worsening, the pre-existing anxiety state.

The symptomatology caused by anxiety and mediated by the automatic nervous system is very varied and can comprise symptoms relating to the cardiovascular system, which can be classified as neurocirculatory asthenia, vasoregulatory asthenia, cardiac neurosis, hyperkinetic heart, a hyperkinetic state, soldier's heart (tachycardia, palpitations, extrasystole, electrocardiographic alterations, lipothymia, precordialgia, arterial pressure, instability, vessel pulsation, etc.), symptoms relating to the respiratory system (dyspnea, sensation of thoracic constriction, etc.), symptoms relating to the locomotive apparatus (hypertonia and muscular rigidity, spasms and muscular clonic jerks, tremors and aches, etc.), symptoms relating to the genitourinary system (palichiuria, polyuria, etc.), symptoms relating to the gastroenteric system (intestinal mobility and secretion disorders) and all other symptoms relating to the autoronic nervous system, such as flushing, pallor, sudation, etc.).

These pathological symptoms are normally treated with psychotrobic agents (anxiolytic drugs), such as the benzodiazepines, which—by acting on the central nervous system—can directly relieve the psychic symptomatology (tension, apprehension, isomnia, anxiety, depressive symptoms, etc.) and undirectly the symptomatology relating to the autonomic nervous system and in most cases only partially; and it is precisely this latter event that causes somatic symptoms resulting from an anxiety state to themselves become not only eziologic agents of the anxiety state but also aggravating factors.

Thus, it is in this perspective that the simultaneous use of psychotropic agents and of beta-adrenergic receptor blocking agents capable of moderating abnormal peripherical responses to catecholamine secretion proves particularly useful.

It has in fact been found that—by administering to a laboratory animal (dog) a composition containing suitable doses of an anxiolytic and of the beta-adrenergic receptor blocking agent—the responses to emotive stress, especially as regards the cardiocirculatory system, can be greatly reduced.

The protective effect thus obtained is not simply the summation of the actions of the two substances but a synergic effect, in that the combination acts simultaneously both on the central nervous system and on adrenergic hypersecretion.

Among the anxiolytic substances, those belonging to the class of the benzodiazepin have shown to be particularly suitable for such purpose, especially 3-N,N-dimethylcarbamoyl-oxy-1-methyl,5-phenyl, 7-chloro,1,3-dihydro-2H-1,4-benzodiazepin-2-one of formula I.

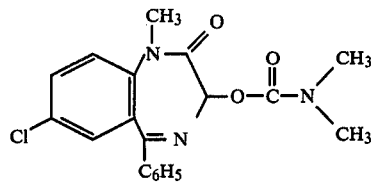

The substance of formula I, the preparation and characteristics of which are described in U.S. Pat. No. 3,867,529, has certain physiological properties which make it particularly suitable for the therapeutical composition according to the present application. These properties can substantially be summed up as having the following aspects: low general toxicity, absence of cardiotoxicity, limited muscle-relaxant effect, limited sleep inducing effect, and also appreciable anxiolytic properties.

Among the beta-adrenergic receptor blocking agents, 1-(o-methoxyphenoxy)-3-isopropylamino-propan-2-ol hydrochloride of formula II proves particularly suitable for the purposes of the therapeutical composition, because of its limited toxicity and also its very highly specific blocking activity.

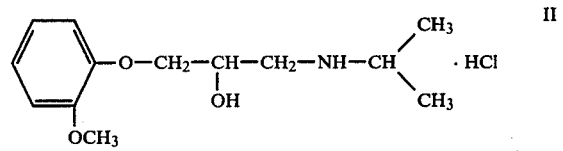

The characteristics of the substance of Formula II which was developed by the Applicants themselves are described, for example, in Arzneimittelforschung (Drug Res.) 20, 1074–79, 1970.

The pharmacologycal results obtained by combining suitable doses of the substance of formula I with that of formula II are reported in the following study, which recapitulates comparative studies in the dog versus administration of similar doses of the single substance with control-grafs of untreated animals.

The studies were performed on 11 conscious mongrel dogs in which were implanted—after appropriate surgery—an electromagnetic flowmeter on the ascending aorta, on the circumflex branch of the left coronary, and a cannula in the carotid vein for flow and arterial pressure measurements so as to allow calculation of the more important hemodynamic parameters.

The studies were carried out according to the following design:

(1) measurement of the parameters in basal conditions and after emotional stress, (2) treated by oral route by means of capsules with the following drugs:

A lactose control, C with substance I, 1 mg/kg, B with substance II 2.5 mg/kg, D with substance I 1 mg/kg++substance II 2.5 mg/kg;

(3) 1 h after the treatment, emotional stress was caused in the dog by sudden spraying of its nose, with 20 ml of ice-cold water and simultaneous firing a single blank from a revolver; at the same time hemodynamic parameters were again measured.

From Table 1, which reports the % variations with respect to the basal values, considered equal to 100, and from Table 2 reporting the statistical analysis of the various data, it can be noted that—on emotional stress——all the hemodynamic parameters are altered in a statistically significant manner (P 0, 01) except the total systemic resistances.

After treatment with II (B) and after stress, the increases in coronary flow and cardiac output are reduced significantly. After treatment with I (C) and after stress, coronary flow, aortic flow and cardiac output are reduced in an equally significant manner; after treatment with the combination I+II (D) and after stress, heart rate, arterial pressure, coronary flow, aortic flow and cardiac output are reduced in a very highly significant manner. Thus, by means of the combination I+II, it is possible to protect the animals from the hemodynamic alterations produced by stress and this action is greater than the summation of the activities of the single drugs; it can therefore be stated that the action of the two drugs is of synergistic type.

It has been found that it is possible to transfer onto the clinical plane the results found in the pharmacological studies. It has in fact been noted that the treatment of certain pathological symptoms of the type identified above can be unexpectedly improved when they are treated with suitable combinations of substances I and II.

It has been found that the suitable doses for the anxiolytic substance of formula I are comprised between 5 and 75 mg; while for the beta-adrenergic receptor blocking agent the suitable doses are between 10 and 100 mg.

In practice, a ratio of the anxiolytic substance and the beta-inhibitor of 1:2.5 proved especially suitable.

The clinical trial carried out with the composition in the above mentioned ratio confirmed the pharmacological premisses, demonstrating that the product provides a sure effect on psychic anxiety symptoms and particularly on somatic anxiety symptoms mediated by the A.N.S., as results from the comparative clinical evaluation, as referred hereunder.

TABLE 1

| | n° esp | Heart rate | Mean arterial pressure | Coronary flow | Coronary resistances | Systolic output | Aortic flow | Cardiac output | Total peripheral resistances |
|---|---|---|---|---|---|---|---|---|---|
| Emotional stress lactose (A) | 29 | 154,9 ± 7,0* | 131,2 ± 3,4* | 165,0 ± 7,5* | 82,5 ± 3,1* | 85,9 ± 3,2* | 128,9 ± 4,6* | 168,8 ± 7,4* | 104,9 ± 5,1 |
| Stress after treatment with substances II (B) 2,5 mg/kg | 14 | 137,5 ± 7,7 | 127,7 ± 3,6 | 134,1 ± 7,2 | 97,9 ± 4,4 | 89,6 ± 4,6 | 119,9 ± 5,9 | 139,6 ± 6,8 | 109,8 ± 6,3 |
| Stress after treatment with substances I (C) 1 mg/kg | 16 | 142,7 ± 6,5 | 125,5 ± 3,7 | 136,9 ± 6,7 | 94,9 ± 4,6 | 82,4 ± 5,2 | 113,9 ± 5,2 | 143,8 ± 7,9 | 114,0 ± 5,8 |
| Stress after treatment with substances I + II (D) 1 mg/kg 25 mg/kg | 21 | 108,1 ± 1,0 | 114,2 ± 2,6 | 108,9 ± 2,9 | 104,9 ± 3,4 | 99,5 ± 0,9 | 107,6 ± 1,4 | 121,7 ± 3,9 | 104,7 ± 2,6 |

*P <0,001

TABLE 2

| A → B | 41 | N.S. | N.S. | P<0,05 | P<0,01 | N.S. | N.S. | P<0,05 | N.S. |
|---|---|---|---|---|---|---|---|---|---|
| A → C | 43 | N.S. | N.S. | P<0,05 | P<0,05 | N.S. | P<0,05 | P<0,05 | N.S. |
| A → D | 48 | P<0,001 | P<0,001 | P<0,001 | P<0,001 | P<0,01 | P<0,001 | P<0,001 | N.S. |

% modification of the hemodynamic parameters caused by the emotional stress given to untreated dogs and kept under control conditions (A), to dogs treated with substance II (B) or upon treatment with substance I (C) or with the two associated drugs (D). The hemodynamic data recorded before the emotional stress were considered equal to 100.

On a case material of 24 patients of both sexes, in the age range between 24 and 55 years, suffering from psychoneurosis with various somatic components, a combination of the compound (I) and compound (II) in the respective dosages of Example No. 1 was tested, in comparison with the two single components of the combination under test.

The patients were evaluated before and after the treatment with Hamilton Scale for the anxiety state. The items of this Scale were divided into two groups, totalling the scores, for the single items before and after the treatment and, more exactly, totalled psychological symptoms (items 1, 2, 3, 4, 5 and 6) and totalled somatic symptoms (items 7, 8, 9, 10, 11 and 12). The total duration of the trial was 15 days and the dosage adopted was established as follows: compound (II) 75 mg in 3 administrations, compound (I) 30 mg in 3 administrations, combination under test of compound (I) 30 mg+compound (II) 75 mg in 3 administrations.

The statistical evaluation was made by means of student's test for the data of the totalled psychological symptoms and totalled somatic symptoms in pairs. Furthermore, the improvement of these two parameters was calculated, i.e. the differences between the scores found before and after the treatment.

The improvements—assessed as mean value of the psychological symptoms and the somatic symptoms were compared by means of general student's test according to the following design: association under test versus compound (I), association under test versus compound (II).

The association under test and compound (I) improve the psychological symptoms in a statically significant manner, whilst compound (II) has scant effect.

As regards the somatic symptoms, all the three drugs proved to be active in a statically significant manner.

Statistical analysis of the improvements obtained with the association as compared to those obtained with the two single components, as regards the psychological symptoms, proves without significance with respect to compound (I), highly significant with respect to compound (II), whilst as regards the somatic symptoms a high statistical significance with respect to both the two single components was noted.

These results allows it to be stated that the association compound (I)+compound (II) makes it possible to act both on more properly so called anxiety symptoms, and on anxiety symptoms mediated by the autonomic nervous system.

Further, these data allow it to be stated that the results of the association of the two drugs are not only the results of a simultaneous action at two levels of attack, but the results of a synergic effect of considerable degree.

cally regulated so as to obtain active plasma levels uniformly valid for the desired times.

It has now been found that a dose of 30 mg of the anxiolytic agent of formula I and 75 mg of the beta adrenergic receptor blocking agent of formula II, suitably formulated in a sustained release form provide a therapeutic protection lasting 10–12 hours with a single administration.

In the following examples two typical formulations according to the present invention are reported in detail. Such examples illustrate, without limiting, the scope of the invention.

EXAMPLE 1

Hard gelatin capsules

| | |
|---|---|
| 7-chloro, 1-methyl, 5-phenyl, 3-dimethylcarbamoyloxy, 1,2-dihydro-3H-1,4 benzodiazepin-2-one | 10 mg |
| 1-(o-methoxyphenoxy)-3-isopropylamino-2-propane-hydrochloride | 25 mg |
| lactose | 165 mg |

100 g of 7-chloro-1-methyl,5-phenyl,3-dimethylcarbamoyloxy-1,2-dihydro-3H-1,4-benzodiazepin-2-one and 250 g of 1-(o-methoxyphenoxy)-3-isopropylamino-2-propanolo hydrochloride and 1,650 kg of lactose are weighed and carefully passed through 20 mesh/cm sieve.

The mixture is placed into a mixer and mixed for 15

|  | A + B (Pz. 8) | | Compound I (A) (Pz. 9) | | Compound (II) (B) (Pz. 7) | | Statistical evaluation | |
|---|---|---|---|---|---|---|---|---|
|  | Before | After | Before | After | Before | After | | |
| Psychological symptoms | 11,00 ± 0,71 | 6,50 ±* 0,27 | 11,55 ± 0,60 | 8,11 ±* 0,56 | 11,14 ± 0,59 | 10,57 ± 0,53 | | |
| Somatic symptoms | 9,62 ± 0,46 | 6,37 ±* 0,18 | 10,00 ± 0,41 | 8,22 ±* 0,46 | 9,71 ± 0,42 | 8,29 ±* 0,36 | | |
| Δ Psychological symptoms improvements | | 4,50 ± 0,68 | | 3,44 ± 0,29 | | 0,57 ± 0,37 | A + B A t = 1,482 n.s. | A + B B t = 4,861 P<0,001 |
| Δ Somatic symptoms improvements | | 3,25 ± 0,37 | | 1,78 ± 0,22 | | 1,43 ± 0,20 | t = 3,549 P<0,01 | t = 4,201 P<0.01 |

Results of the double blind studies carried out on 3 groups of patients treated with compound I (A), compound II (B) and the asociation A + B. Mean values ± s.e. of the totalled psychological symptoms and the totalled somatic symptoms are reported, obtained before and after the treatment with statistical evaluation my means of Student's test for paired data. Also, mean values ± s.e. of the degree of improvement of the psychlogical symptoms and somatic symptoms are reported, together with statistical evaluation by means of general Student's test according to the following design: A + B → A; A + B → B.

The dosage forms of the therapeutical composition here described can be prepared according to the customary known art.

As the dosage forms are for oral administration, the active ingredients—such as for example those of the substances of formula I and II in the above identified reciprocal proportions are mixed with excipients, lubricants, disintegrating agents and additional substances normally acceptable for pharmaceutical use, in order to obtain hard or soft gelatin capsules, tablets or sugar-coated tablets.

Such substances comprise starch, microcrystalline cellulose, silica, alkaline and alkaline earth metal posphates, talc, polyoxyethylene glycols of various molecular weight, gelatin, kaolin, magnesium stearate, sorbitan monooleates, alginic acid, etc.

Oral sustained release dosage forms can also be obtained according to the known art for such preparations, for example as described in "Controlled Action Drug Forms", J. C. Colbert, Noyes Data Corp/Parke Ridge, N.J., London (1974). The doses of the two active principles in this type of preparation should be reciprocally regulated so as to obtain active plasma levels uniformly valid for the desired times.

minutes. The mixture is analyzed to verify the homogeneous dispersion of the active principles in the excipients. The capsules are metered and filled to 200 mg each, with a capsule-filling machine. The weight of the capsules is controlled every 30 minutes.

EXAMPLE 2

Sustained release capsules

Each capsule contains:

| | |
|---|---|
| (1) 3-N,N-dimethylcarbamoyloxy-1-methyl,5-phenyl, 7-chloro, 1,3-dihydro-2H-1,4-benzodiazepin-2-one | 30 mg |
| (2) 1-(o-methoxyphenoxy)-3-isopropylamino-propan-2-ol | 75 mg |
| (3) sucrose | 129.9 mg |
| (4) starch | 54.3 mg |
| (5) stearic acid | 0.8 mg |
| (6) polyvinylpyrrolidone | 2.00 mg |
| (7) methacrylic acid polymers | 2.3 mg |
| (8) talc | 25.7 mg |

In a suitable machine, for centrifugal extrusion, microspheres are prepared by utilizing a hot mixture of sucrose, starch and water. The microspheres are dried in hot air and then sieved, collecting only those with a diameter corresponding to 8 mesh.

In a coating pan the active principle (1) is applied to a part of the microspheres added to stearic acid, utilizing an adhesive solution prepared with water and a part of the polyvinylpyrrolidone. The microspheres are dried in a current of hot air. Subsequently to the microspheres with the said active principle, a second layer is applied by means of a treatment with a varnish prepared with the polymers of esters of the methacrylic acid and talc. Release over time depends on the number of applied layers of such varnish on the microspheres with the active principle.

The application of the varnish is in each case carried out in the coating pan by means of a suitable sprayer.

Part of the microspheres without varnish serves for the immediate release portion of the composition.

A similar procedure is carried out on the proportional part of sucrose granules left aside and destined to incorporate the active principle, (2).

Once the granules with applied varnish formine the membrane for controlled release have been obtained, the microgranules of each single type are mixed, operating as to obtain the following release rates:

(1) for the active principle (1), by hour 1 30%, by our 2 60%, by hour 6 100%.

(2) for the active principle (2), the same percentages of release at the same time as for the active principle (1).

Finally, suitable amounts of granules as under (1) and of those as under (2) are mixed sp as to provide a mixture which on analysis contains 30 mg of the active principle as under (1), 7.5 mg of the active principle as under (2).

With such mixture, hard gelatin capsules size No. 2 are filled. Each capsule contains 320 mg of granules.

What we claim is:

1. A pharmaceutical composition in a form suitable for oral administration for the therapeutic treatment of anxiety and neurodystonic states comprising the benzodiazepine anxiolytic dimethylcarbamoyloxy-1-methyl-5-phenyl-7-chloro-1,3-dihydro-2H-1,4-benzodiazepin-2-one and the beta-adrenergic receptor blocking agent 1-(o-methoxyphenoxy)-3-isopropylamino- propan-2-ol, the ratio of the benzodiazepine anxiolytic to beta-adrenergic receptor blocking agent being from 5 to 75 parts by weight: 10 to 100 parts by weight.

2. A composition according to claim 1, characterized by the fact that the the dosage of the anxyolitic is comprised in the range of from 5 to 75 mg whilst the dosage of the blocking agent is in the range of from 10 to 100 mg.

3. A composition according to claim 2 wherein the ratio of benzodiazepine anxyolitic to blocking agent is 1:2.5.

4. A composition according to claim 1, characterized by the fact that it is in a sustained release form.

5. A composition according to claim 4, characterized by the fact that it is formulated so as to have for both the active principles a 30% release by hour 1, a 60% release by hour 4, and 100% release by hour 6.

6. A composition according to claim 3 containing 30 mg of benzodiazepine anxyolitic and 75 mg of blocking agent.